(12) United States Patent
Upton et al.

(10) Patent No.: US 10,273,272 B2
(45) Date of Patent: Apr. 30, 2019

(54) ANTIMICROBIAL PEPTIDES

(71) Applicant: Amprologix Limited, Plymouth (GB)

(72) Inventors: Mathew Upton, Plymouth (GB);
Samantha Halliwell, Manchester (GB);
Jeremy Derrick, Manchester (GB)

(73) Assignee: Amprologix Limited, Plymouth (GB)

( * ) Notice: Subject to any disclaimer, the term of this patent is extended or adjusted under 35 U.S.C. 154(b) by 0 days.

(21) Appl. No.: 15/123,155

(22) PCT Filed: Mar. 2, 2015

(86) PCT No.: PCT/GB2015/050601
§ 371 (c)(1),
(2) Date: Sep. 1, 2016

(87) PCT Pub. No.: WO2015/132572
PCT Pub. Date: Sep. 11, 2015

(65) Prior Publication Data
US 2017/0204146 A1    Jul. 20, 2017

(30) Foreign Application Priority Data

Mar. 4, 2014    (GB) .................................. 1403794.9

(51) Int. Cl.
| | | |
|---|---|---|
| A61K 38/00 | (2006.01) |
| A61K 38/04 | (2006.01) |
| C07K 5/00 | (2006.01) |
| C07K 16/00 | (2006.01) |
| C07K 17/00 | (2006.01) |
| A61K 38/10 | (2006.01) |
| A61K 38/16 | (2006.01) |
| C09K 3/00 | (2006.01) |
| C07K 14/31 | (2006.01) |
| C07K 7/08 | (2006.01) |
| A61K 6/00 | (2006.01) |

(52) U.S. Cl.
CPC .............. *C07K 14/31* (2013.01); *A61K 38/10* (2013.01); *C07K 7/08* (2013.01); *A61K 6/00* (2013.01); *A61K 38/00* (2013.01)

(58) Field of Classification Search
None
See application file for complete search history.

(56) References Cited

FOREIGN PATENT DOCUMENTS

| WO | WO-99/06440 A1 | 2/1999 |
| WO | WO-2011/073663 A1 | 6/2011 |

OTHER PUBLICATIONS

Thundimadathil, Drug Delivery & Development Magazine, available online at https://www.dddmag.com/article/2013/02/drug-delivery-using-cell-penetrating-peptides, 7 pages (2013) (Year: 2013).*
Dhople et al., "Conformation and activity of delta-lysin and its analogs," Peptides, Feb. 2005, vol. 26, No. 2, pp. 217-225.
Gibreel et al., "Synthetic epidermicin NI01 can protect *Galleria mellonella* larvae from infection with *Staphylococcus aureus*," Journal of Antimicrobial Chemotherapy, May 27, 2013, vol. 68, No. 10, pp. 2269-2273.
Gonzalez et al., "Bacteriocin AS-48, a microbial cyclic polypeptide structurally and functionally related to mammalian NK-lysin," PNAS, Oct. 10, 2000, vol. 97, No. 21, pp. 11221-11226.
International Search Report and Written Opinion dated May 8, 2015, in the International Application No. PCT/GB2015/050601 filed on Mar. 2, 2015, 12 pages.
Jiang et al., "Effects of Net Charge and the Number of Positively Charged Residues on the Biological Activity of Amphipathic α-Helical Cationic Antimicrobial Peptides," Biopolymers, Author manuscript available in PMC Oct. 13, 2009 (24 pages), published earlier in Biopolymers, 2008, vol. 90, No. 3, 369-383.
Sandiford et al., "Identification, Characterization, and Recombinant Expression of Epidermicin NI01, a Novel Unmodified Bacteriocin Produced by *Staphylococcus epidermidis* That Displays Potent Activity against *Staphylococci*," Antimicrobial Agents and Chemotherapy, Mar. 2012, vol. 56, No. 3, pp. 1539-1547.
UK Combined Search and Examination Report dated Nov. 20, 2015, in United Kingdom Application No. GB1503483.8, 10 pages.
UK Search Report dated Nov. 27, 2014, in United Kingdom Application No. GB1403794.9, 5 pages.
Wu et al., "Interaction of the Cyclic Antimicrobial Cationic Peptide Bactenecin with the Outer and Cytoplasmic Membrane", The Journal of Biological Chemistry, vol. 274, No. 1 Issue of Jan. 1, 1999, pp. 29-35.

* cited by examiner

*Primary Examiner* — James H Alstrum-Acevedo
*Assistant Examiner* — Thea D' Ambrosio
(74) *Attorney, Agent, or Firm* — Wilmer Cutler Pickering Hale and Dorr LLP (57) ABSTRACT

The present invention provides novel antimicrobial peptides and nucleic acids encoding them, the peptides having an inhibitory or bactericidal/bacteriostatic effect on both Gram-negative and Gram-positive bacteria. The invention includes methods of treating bacterial infections and preventing the spread of the infections or contamination by the infection. The peptides of the present invention are of particular use as therapeutics to treat Gram-negative infections and are of use in impregnation, covering or coating medical devices or implants or prosthetics prior to introduction into a patient's body.

10 Claims, 4 Drawing Sheets
Specification includes a Sequence Listing.

| | | |
|---|---|---|
| NIO1₁₋₅₁ | MAAFMKLIQFLATKGQKYVSLAWKHKGTILKWINAGQSFEWIYKQIKKLWA | (SEQ ID NO:10) |
| NIO1₁₋₃₇ | MAAFMKLIQFLATKGQKYVSLAWKHKGTILKWINAGQ | (SEQ ID NO:11) |
| NIO1₃₈₋₅₁ | SFEWIYKQIKKLWA | (SEQ ID NO:12) |
| NIO1₆₋₄₈ | KLIQFLATKGQKYVSLAWKHKGTILKWINAGQSFEWIYKQIKK | (SEQ ID NO:13) |
| NIO1₁₄₋₅₁ | KGQKYVSLAWKHKGTILKWINAGQSFEWIYKQIKKLWA | (SEQ ID NO:14) |
| NIO1₁₆₋₅₁ | KYVSLAWKHKGTILKWINAGQSFEWIYKQIKKLWA | (SEQ ID NO:15) |
| NIO1₂₃₋₅₁ | KHKGTILKWINAGQSFEWIYKQIKKLWA | (SEQ ID NO:16) |
| NIO1₂₅₋₅₁ | KGTILKWINAGQSFEWIYKQIKKLWA | (SEQ ID NO:17) |
| NIO1₃₀₋₅₁ | KWINAGQSFEWIYKQIKKLWA | (SEQ ID NO:18) |
| NIO1₄₄₋₅₁ | KQIKKLWA | (SEQ ID NO:19) |

SEQUENCE LISTING

<160> NUMBER OF SEQ ID NOS: 23

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Ser Phe Glu Trp Ile Tyr Lys Gln Ile Phe Lys Leu Trp Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

```
<400> SEQUENCE: 2

Ser Phe Glu Trp Ile Lys Tyr Gln Ile Lys Lys Leu Trp Ala
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Ser Phe Glu Trp Ile Tyr Lys Gln Ile Trp Lys Leu Lys Arg Gly Leu
1               5                   10                  15

Ala

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Ser Phe Lys Trp Ile Tyr Lys Gln Ile Lys Lys Leu Trp Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide

<400> SEQUENCE: 5

Ser Phe Lys Trp Ile Tyr Lys Gln Ile Lys Lys Leu Trp Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Ser Phe Glu Trp Ile Tyr Lys Gln Ile Lys Lys Leu Trp Ala Lys
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Ser Phe Glu Trp Ile Tyr Lys Gln Ile Lys Lys Leu Trp Ala Lys Lys
1               5                   10                  15

Lys

<210> SEQ ID NO 8
<211> LENGTH: 14
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be leucine or isoleucine
<220> FEATURE:
<221> NAME/KEY: misc_feature
<222> LOCATION: (9)..(9)
<223> OTHER INFORMATION: Xaa can be leucine or isoleucine
<220> FEATURE:
<221> NAME/KEY: misc_feature
<222> LOCATION: (12)..(12)
<223> OTHER INFORMATION: Xaa can be leucine or isoleucine

<400> SEQUENCE: 8

Ser Phe Glu Trp Xaa Tyr Lys Gln Xaa Lys Lys Xaa Trp Ala
1               5                   10

<210> SEQ ID NO 9
<211> LENGTH: 15
<212> TYPE: PRT
<213> ORGANISM: Staphylococcus epidermidis

<400> SEQUENCE: 9

Gln Ser Phe Glu Trp Ile Tyr Lys Gln Ile Lys Lys Leu Trp Ala
1               5                   10                  15

<210> SEQ ID NO 10
<211> LENGTH: 51
<212> TYPE: PRT
<213> ORGANISM: Staphylococcus epidermidis

<400> SEQUENCE: 10

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln Ser Phe Glu Trp Ile Tyr Lys Gln Ile Lys Lys
        35                  40                  45

Leu Trp Ala
    50

<210> SEQ ID NO 11
<211> LENGTH: 37
<212> TYPE: PRT
<213> ORGANISM: Staphylococcus epidermidis

<400> SEQUENCE: 11

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln
        35

<210> SEQ ID NO 12
<211> LENGTH: 14
<212> TYPE: PRT
<213> ORGANISM: Staphylococcus epidermidis

<400> SEQUENCE: 12

Ser Phe Glu Trp Ile Tyr Lys Gln Ile Lys Lys Leu Trp Ala
1               5                   10
```

```
<210> SEQ ID NO 13
<211> LENGTH: 43
<212> TYPE: PRT
<213> ORGANISM: Staphylococcus epidermidis

<400> SEQUENCE: 13

Lys Leu Ile Gln Phe Leu Ala Thr Lys Gly Gln Lys Tyr Val Ser Leu
1               5                   10                  15

Ala Trp Lys His Lys Gly Thr Ile Leu Lys Trp Ile Asn Ala Gly Gln
            20                  25                  30

Ser Phe Glu Trp Ile Tyr Lys Gln Ile Lys Lys
        35                  40

<210> SEQ ID NO 14
<211> LENGTH: 38
<212> TYPE: PRT
<213> ORGANISM: Staphylococcus epidermidis

<400> SEQUENCE: 14

Lys Gly Gln Lys Tyr Val Ser Leu Ala Trp Lys His Lys Gly Thr Ile
1               5                   10                  15

Leu Lys Trp Ile Asn Ala Gly Gln Ser Phe Glu Trp Ile Tyr Lys Gln
            20                  25                  30

Ile Lys Lys Leu Trp Ala
        35

<210> SEQ ID NO 15
<211> LENGTH: 35
<212> TYPE: PRT
<213> ORGANISM: Staphylococcus epidermidis

<400> SEQUENCE: 15

Lys Tyr Val Ser Leu Ala Trp Lys His Lys Gly Thr Ile Leu Lys Trp
1               5                   10                  15

Ile Asn Ala Gly Gln Ser Phe Glu Trp Ile Tyr Lys Gln Ile Lys Lys
            20                  25                  30

Leu Trp Ala
        35

<210> SEQ ID NO 16
<211> LENGTH: 28
<212> TYPE: PRT
<213> ORGANISM: Staphylococcus epidermidis

<400> SEQUENCE: 16

Lys His Lys Gly Thr Ile Leu Lys Trp Ile Asn Ala Gly Gln Ser Phe
1               5                   10                  15

Glu Trp Ile Tyr Lys Gln Ile Lys Lys Leu Trp Ala
            20                  25

<210> SEQ ID NO 17
<211> LENGTH: 26
<212> TYPE: PRT
<213> ORGANISM: Staphylococcus epidermidis

<400> SEQUENCE: 17

Lys Gly Thr Ile Leu Lys Trp Ile Asn Ala Gly Gln Ser Phe Glu Trp
1               5                   10                  15

Ile Tyr Lys Gln Ile Lys Lys Leu Trp Ala
            20                  25
```

```
<210> SEQ ID NO 18
<211> LENGTH: 21
<212> TYPE: PRT
<213> ORGANISM: Staphylococcus epidermidis

<400> SEQUENCE: 18

Lys Trp Ile Asn Ala Gly Gln Ser Phe Glu Trp Ile Tyr Lys Gln Ile
1               5                   10                  15

Lys Lys Leu Trp Ala
            20

<210> SEQ ID NO 19
<211> LENGTH: 8
<212> TYPE: PRT
<213> ORGANISM: Staphylococcus epidermidis

<400> SEQUENCE: 19

Lys Gln Ile Lys Lys Leu Trp Ala
1               5

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide

<400> SEQUENCE: 20

Ser Phe Glu Trp Ile Tyr Lys Gln Pro Lys Lys Leu Trp Ala
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide

<400> SEQUENCE: 21

Ser Phe Lys Trp Ile Tyr Lys Gln Pro Lys Lys Leu Trp Ala
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide

<400> SEQUENCE: 22

Ser Phe Lys Trp Pro Tyr Lys Gln Ile Lys Lys Leu Trp Ala
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Ser Phe Lys Trp Ile Tyr Lys Gln Pro Lys Lys Leu Trp Ala Lys Lys
1               5                   10                  15

Lys
```

ANTIMICROBIAL PEPTIDES

REFERENCE TO RELATED APPLICATIONS

This Application is a national Stage Entry of PCT International Application No. PCT/GB2015/050601 filed Mar. 2, 2015, which claims priority to GB1403794.9, filed Mar. 4, 2014, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 29, 2017, is named 2017-03-29 138 US1 Sequence Listing.txt and is 7,073 bytes in size.

The present invention relates to novel antimicrobial peptides and nucleic acids encoding them, the peptides having an inhibitory or bactericidal effect on both Gram-negative and Gram-positive bacteria. The invention includes inter alia methods of treating bacterial infections and preventing the spread of the infections or contamination by the infectious agent. The peptides of the present invention are of particular use as therapeutics to treat Gram-negative infections and are of use in impregnation, covering or coating medical devices, implants or prosthetics prior to introducing them into a patient's body.

BACKGROUND

Gram negative bacterial cell walls are more complex than Gram positive bacterial cell walls, both structurally and chemically. Structurally, a Gram negative cell wall contains two layers external to the cytoplasmic membrane, the outer membrane is like a stiff canvas sack around the bacteria. The outer membrane maintains the bacterial structure and is a permeability barrier to large molecules and hydrophobic molecules. It also provides protection from adverse environmental conditions such as the digestive system of a host (important for Enterobacteriaceae organisms). Compared with Gram-positive bacteria, Gram-negative bacteria are more resistant against antibodies and detergents. In general, Gram positive bacteria tend to persist in dry environments better and are often found on places like the skin and in dust. Gram negative bacteria, on the other hand, are killed more quickly by drying but thrive in aqueous environments. Gram negative bacteria also tend to grow better in the presence of toxic chemicals (such as chlorine), a feat thought to be enabled by their two cell membranes and which is especially problematic in the health care environment.

Gram-negative bacteria cause a variety of pathological conditions including pneumonia, bloodstream infections, wound or surgical site infections, sexually transmitted diseases including gonorrhea, and meningitis. Gram-negative bacteria are resistant to multiple drugs and are increasingly resistant to most available antibiotics. Certain types of Gram-negative bacteria have become increasingly resistant to available antibiotic drugs. Some strains are now resistant to many, most, or all available treatments resulting in increased illness and death from bacterial infections, and contributing to escalating healthcare costs. Examples of Gram-negative bacteria that have demonstrated drug resistance include:

E. coli, which causes the majority of urinary tract infections and healthcare associated blood stream infections.

Acinetobacter baumanii, which causes disease mainly in healthcare settings.

Pseudomonas aeruginosa, which causes bloodstream infections and pneumonia in hospitalized patients.

Klebsiella pneumoniae, which causes many types of healthcare-associated infections, including pneumonia, urinary tract infections, and bloodstream infections Neisseria gonorrhoeae, which causes the sexually transmitted infection gonorrhea.

Gram-negative bacteria can cause many types of infections and are spread to humans in a variety of ways. Several species, including Escherichia coli, are common causes of food-borne disease. Virulent strains of E. coli can cause gastroenteritis, urinary tract infections, and neonatal meningitis. In rarer cases, virulent strains are also responsible for hemolytic-uremic syndrome, peritonitis, mastitis, septicemia and Gram-negative pneumonia.

K. pneumoniae can cause pneumonia and can cause destructive changes to human lungs, inflammation and hemorrhage with necrosis. Typically these bacteria gain access after a person aspirates colonizing oropharyngeal microbes into the lower respiratory tract. The most common infection caused by Klebsiella bacteria outside the hospital is pneumonia, typically in the form of bronchopneumonia and also bronchitis. These patients have an increased tendency to develop lung abscess, cavitation, empyema, and ural adhesions. The disease has an alarmingly high death rate of about 50% even with antimicrobial therapy and the mortality rate can be nearly 100% for persons other compromising conditions such as with alcoholism and bacteremia. Within the healthcare setting, nosocomial pneumonia is the second-most-common nosocomial infection, the disease adds significantly to the cost of hospital care and to the length of hospital stays.

In addition to pneumonia, Klebsiella can also cause infections in the urinary tract, lower biliary tract, and surgical wound sites. The range of clinical diseases includes pneumonia, thrombophlebitis, urinary tract infection (UTI), cholecystitis, diarrhea, upper respiratory tract infection, wound infection, osteomyelitis, meningitis, and bacteremia. If a person has an invasive device in their body then contamination of the device becomes a risk; for example respiratory support equipment and urinary catheters put patients at increased risk. Also, the use of antibiotics can be a factor that increases the risk of nosocomial infection with Klebsiella bacteria.

Of the Gram-positive bacteria, S. epidermidis is usually non-pathogenic, however these bacteria are responsible for a growing number of infections among hospital patients whose immune systems are weakened or compromised and in immuno-competent individuals with indwelling medical devices. Such infections often occur because the bacterium is carried from the surface of the skin to deeper tissues and the blood stream by insertion of venous catheters or peritoneal dialysis catheters. These infections can be both nosocomial or community acquired, but they are more of a threat to hospital patients. This is in part due to hospitals harboring more virulent strains of the organism and the continuous use of antibiotics and disinfectants. S. epidermidis is a major concern for individuals with catheters or other surgical implants because it is known to cause biofilms that grow on such devices, especially on intravenous catheters and on medical prostheses. Infection can also occur in dialysis patients or anyone with an implanted medical device that may have been contaminated. S. epidermidis has also been associated with endocarditis and occurs most frequently in patients with defective heart valves. It is also responsible for the majority of late-onset sepsis in newborns.

To survive during colonization or infection of the human body, microorganisms must circumvent mechanisms of innate host defense. Antimicrobial peptides (also known as natural antibiotics) represent a key component of innate host defense, especially in phagocytes and on epithelial surfaces. Antimicrobial peptides derived from humans and other higher animals are potent, broad-spectrum antibiotics and those of bacterial origin tend to have a more focused spectrum of activity. Both types of peptide demonstrate potential as alternative novel therapeutic agents. The interaction of the peptides with susceptible cells is thought to occur via ionic interactions and results in cell death by destabilization of the membranes and/or pore formation. Epidermicin is a bactericidal peptide with rapid and potent activity against a wide range of gram-positive pathogens.

WO2011/073663 describes the identification, purification, characterization and expression of epidermicin, an antimicrobial peptide which is an unmodified or native bacteriocin produced by Staphylococcus epidermidis strain 224. The natural peptide of WO2011/073663 is a highly cationic, hydrophobic, plasmid-encoded peptide that exhibits potent antimicrobial activity toward a wide range of pathogenic Gram-positive bacteria including methicillin-resistant Staphylococcus aureus (MRSA), enterococci, and biofilm-forming S. epidermidis strains.

However, the increasing resistance of bacteria to many synthetic antibiotics emphasizes the urgent need for new and more effective antimicrobial agents. There is a need for new and effective preventive and therapeutic treatments for bacterial infections, especially against Gram-negative bacterial infections and ideally in conjunction with the ability to also concomitantly treat Gram-positive infections.

BRIEF SUMMARY OF THE DISCLOSURE

According to a first aspect of the invention there is provided an isolated or recombinant peptide comprising a sequence selected from the group comprising SFEWIYKQIFKLWA [SEQ ID NO:1], SFEWIKYQIKKLWA [SEQ ID NO:2], SFEWIYKQIWKLKRGLA [SEQ ID NO:3], formyl-SFKWIYKQIKKLWA [SEQ ID NO:4], SFKWIYKQIKKLWA [SEQ ID NO:5], SFEWIYKQIKKLWA [SEQ ID NO:6], SFEWIYKQIKKLWAKKK [SEQ ID NO:7] and SFEWXYKQXKKXWA [SEQ ID NO:8] wherein X is leucine or isoleucine, or sequences having at least 90% identity to any one of sequences SEQ ID NO:1 to SEQ ID NO:8, wherein the isolated or recombinant peptides are bactericidal and/or bacteriostatic.

Preferably, the peptides of the present invention are bactericidal and/or bacteriostatic against both Gram-negative and Gram-positive bacteria and more preferably are bactericidal against Gram-negative bacteria. The peptides of the present invention are modified versions of the natural or native epidermicin peptide.

According to a further aspect of the invention there is provided an isolated or recombinant nucleic acid sequence comprising a sequence encoding a peptide comprising a sequence selected from the group comprising SFEWIYKQIFKLWA [SEQ ID NO:1], SFEWIKYQIKKLWA [SEQ ID NO:2], SFEWIYKQIWKLKRGLA [SEQ ID NO:3], formyl-SFKWIYKQIKKLWA [SEQ ID NO:4], SFKWIYKQIKKLWA [SEQ ID NO:5], SFEWIYKQIKKLWA [SEQ ID NO:6], SFEWIYKQIKKLWAKKK [SEQ ID NO:7] and SFEWXYKQXKKXWA [SEQ ID NO:8] wherein X is leucine or isoleucine or sequences having at least 90% identity to any one of sequences SEQ ID NO:1 to SEQ ID NO:8, wherein the isolated or recombinant peptides are bactericidal and/or bacteriostatic.

According to a yet further aspect of the invention there is provided a peptide or nucleic acid encoding the said peptide as herein before described wherein the peptide has an inhibitory effect on biofilm formation by a biofilm-producing bacterium.

According to a yet further aspect of the invention there is provided a pharmaceutical composition comprising any one or more of the peptides as herein before described.

According to a yet further aspect of the invention there is provided an item impregnated with or coated in or covered by one or more peptides of the present invention, the item being selected from the group comprising a medical device, medical instrument, medical implement, prosthetic, catheter, implantable device or material or tissue and a wound dressing or any other medical or dental device which could be implanted into or come into contact with a patient and especially a patient's blood.

According to a yet further aspect of the invention there is provided a biologically compatible material selected from the group comprising cement, glue, composite, tissue matrix or scaffold or wound dressing incorporating or impregnated with the peptides of the present invention.

According to a yet further aspect of the invention there is provided a dental preparation comprising the peptides as herein before described.

According to a yet further aspect of the invention there is provided a pharmaceutical composition comprising any one or more of the peptides of the present invention and an excipient, carrier or diluent.

It will be appreciated that in some embodiments of the invention a mixture of peptides may be selected according to their bactericidal activity or potency and depending on the infection that is to be treated. Advantageously the peptides of the present invention provide a wider range of antibacterial agents since they possess both Gram positive and Gram negative activity and can be used as designer antibiotics.

Any features ascribed to one of the aspects of the invention apply mutatis mutandis to each and every aspect of the invention.

BRIEF DESCRIPTION OF THE DRAWINGS AND TABLES

Embodiments of the invention are further described hereinafter with reference to the accompanying drawings, in which.

Table 1 shows the minimum inhibitory concentrations (MIC) of epidermicin fragments of the full length protein against a range of Gram-positive pathogens.

Table 2 shows the minimum inhibitory concentrations (MIC) of epidermicin derivatives and the peptides of the present invention against a range of Gram-positive and negative pathogens.

Table 3 shows modifications of peptides of the present invention as compared to SEQ ID NO:9.

Table 4 shows the percentage identity of the most similar and most dissimilar peptides as compared to SEQ ID NO:9

Table 5 shows the average MIC Data (ug/ml) for epidermicin derivative peptides of the present invention against *E. coli* and *K. pneumonia*.

Table 6 shows the effect of increased charge on haemolysis.

DETAILED DESCRIPTION

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The term "peptide" refers to a polymer of amino acid residues. The term apply to amino acid polymers in which one or more amino acid residue is an artificial chemical mimetic of a corresponding naturally occurring amino acid, as well as to naturally occurring amino acid polymers and non-naturally occurring amino acid polymers.

A "variant" peptide comprises a peptide sequence that differs in one or more amino acid residues from the peptide sequence of a parent or reference peptide (such as, e.g., a wild-type (WT) peptide sequence). In one aspect, a variant peptide comprises a peptide sequence which differs from the peptide sequence of a parent or reference peptide in from about 5%, 10%, 15%, 20%, 30% 40%, 50% or more of the total number of residues of the parent or reference peptide sequences. In another aspect, a variant peptide comprises a peptide sequence that has at least about 50%, 60%, 70%, 80% or 90% sequence identity to the peptide sequence of a parent or reference peptide. In another aspect, a variant peptide comprises a peptide sequence that differs from the peptide sequence of a parent or reference peptide in from 1 to 10 or more amino acid residues (e.g., 1, 2, 3, 4, 5, 6, 7, 8, 9 or 10). A variant peptide may comprise a peptide sequence that differs from the peptide sequence of a parent or reference peptide by, e.g., the deletion, addition, or substitution of one or more amino acid residues (e.g., 1, 2, 3, 4, 5, 6, 7, 8, 9 or 10) of the parent or reference peptide, or any combination of such deletion(s), addition(s), and/or substitution(s). The reference or parent peptide may itself be a variant peptide.

A nucleic acid or peptide is "recombinant" when it is artificial or engineered, or derived from an artificial or engineered protein or nucleic acid.

As used herein, "sequence identity" or "identity" in the context of two polynucleotides or peptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Certain variant peptides encompassed by the present invention are biologically active, that is, they continue to possess the desired biological activity i.e. bacteriocidal and/or bacteriostatic, as described herein. Biologically active variants of the peptides of the present invention will have at least about 40%, 45%, 50%, 55%, 60%, 65%, 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequences as determined by sequence alignment programs and parameters.

The invention features peptides, preferably substantially pure preparations of peptides, or recombinant peptides. In preferred embodiments: the peptide has biological activity; the peptide has an amino acid sequence at least 55%, 60%, 65%, 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more identical to an amino acid sequence of the invention as depicted in any one of SEQ ID NOs:1 or 8, preferably it has about 65% sequence identity with an amino acid sequence, and most preferably it has about 90% to about 95% sequence identity with an amino acid sequence of the invention. The peptide is at least 7, 8, 9, 10, 11, 12, 13, 14, 15, 16, 17 or more amino acid residues in length; the peptide includes at least 10 and more preferably at least 14 or more contiguous amino acid residues of the invention contained in the Sequence Listing.

The peptides of the present invention are bactericidal and/or bacteriostatic that is to say they are capable of preventing infection by inhibiting the growth or action of Gram positive and Gram negative microorganisms by for example killing or destroying bacteria and/or or they may have an inhibitory effect on biofilm formation by a biofilm-producing bacterium or they may simply inhibit bacterial colonisation. The peptides of the present invention advantageously provide a broad spectrum of anti-bacterial activity, especially when provided as a mixture of peptides.

A "biofilm" is a complex organization of bacteria that are anchored to a surface via a bacterially extruded exopolymeric matrix, and grow into differentiated micro-colonies. The extruded exopolymeric matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because of a lack of accessibility by immunoglobulin and complement. The attachment of bacteria to a surface triggers the expression of a cassette of genes, which results in the formation of a biofilm. A "biofilm phenotype" confers to a bacterium possessing a reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and cellular surfaces.

The target of epidermicin is likely to be the inner membrane, which both Gram positives and negatives possess. However, the full length peptide (SEQ ID NO:10) was found not to be have potent activity against Gram negative cells (data not shown) so it was unexpected to find that any derivatives or fragments were capable of traversing the outer membrane and accessing the inner membrane. It was a most surprising finding that the truncated and modified novel peptides of the present invention based on the epidermicin peptide were effective against Gram negative bacteria. It is by no means predictable that shorter peptides of epidermicin would be able to access the inner membrane of Gram negatives, especially since they were found to be refractory to epidermicin. Furthermore, it has been clearly demonstrated that some sequence modifications abolish (or significantly diminish) activity (Table 3).

Preferably the peptides of the present invention are "inhibitory" that is to say they prevent or reduce the bacteria's ability to grow or form biofilms. Biofilms have been found to be involved in a wide variety of microbial infections in the body. Infectious processes in which biofilms have been implicated include common problems such as urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves. More recently it has been noted that bacterial biofilms may impair cutaneous wound healing and reduce topical antibacterial efficiency in healing or treating infected skin wounds. As regards dental plaque, this is the material that adheres to the teeth and consists of bacterial cells (mainly the Gram positive *Streptococcus mutans* and *Streptococcus sanguinis*), salivary polymers and bacterial extracellular products. Plaque is a biofilm on the surfaces of the teeth and accumulation of microorganisms subject the teeth and gingival tissues to high concentrations of bacterial metabolites which results in dental disease. Furthermore, Gram negative *Legionella* bacteria are known to grow under certain conditions in biofilms, in which they are protected against disinfectants. Workers in cooling towers, persons working in air conditioned rooms and people taking a shower are exposed to *Legionella* by inhalation when the systems are not well designed, constructed, or maintained.

Preferably the Gram negative bacterial infections that can be treated by the peptides of the present invention are selected from the group comprising Enterobacteriales, Bacteriodales, Legionellales, Neisseriales, Pseudomonales, Vibrionales, Pasterrellales and Camylobacterales.

Preferably, the bacterial infection is as a result of an infection caused by, but not limited to, the following bacteria selected from the group comprising *Acinetobacter, Actinobacillus, Bordetella, Brucella, Campylobacter, Cyanobacteria, Enterobacter, Erwinia, Escherichia coli, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio* and *Yersinia* species. More preferably the infection is a as a result of *E. coli, Klebsiella pneumonia, Acinetobacter baumanii, Pseudomonas aeruginosa, Neisseria gonorrhoeae* or *Neisseria* meningitis.

Preferably the Gram positive bacterial infections that can be treated by the peptides of the present invention are selected from the group comprising *Staphylococcus, Streptococcus, Enterococcus* (including Vancomycin-resistant *Enterococcus faecalis*: VRE), *Bacillus* and *Listeria*.

Preferably, the bacterial infection is as a result of an infection caused by, but not limited to, the following bacteria selected from the group comprising *Staphyloccus saprophyticus, Staphyloccocus xylosus, Staphyloccocus lugdunensis, Staphyloccocus schleiferi, Stapylococcus caprae, Staphylococcus epidermidis, Staphylococcus hominis, Staphylococcus saprophyticus, Staphylococcus warneri, Staphylococcus aureus,* MRSA, *Enterococcus faecalis, Enterococcus faecium* (including Vancomycin-resistant enterococcus VRE), *Proprionibacterium acnes, Bacillus cereus, Bacillus subtilis, Listeria monocytogenes, Streptococcus pyogenes, Streptococcus salivarius, Streptococcus mutans* or *Streptococcus pneumoniae* and more preferably is as a result of a *Staphylococcus aureus* infection.

The present invention also provides a method of killing or damaging bacteria. The method involves contacting the bacteria with the antimicrobial peptides of the present invention. In some instances, the bacteria will be killed outright, and signs or symptoms of bacterial colonization or infection will be completely eradicated. However, those of skill in the art will recognize that much benefit can be derived even if all bacteria in a population are not killed outright. For example, in some cases, the ability of the bacteria to carry out metabolic reactions may be slowed or otherwise attenuated by exposure to the antimicrobial peptides, or the reproductive potential of the bacteria may be decreased. All such lessening of the bacteria's ability to flourish in an environment in which they would typically establish colonies and biofilms and persist may be of benefit to a host organism in need of treatment with the antimicrobial peptides of the invention.

While in one embodiment of the invention, treatment of bacterial host organisms or potential bacterial host organisms is contemplated (e.g. humans and other mammals, so that veterinary uses are also included), other uses of the antimicrobial peptides of the invention will also occur to those of skill in the art. For example and without limitation, the treatment of surfaces of synthetic or natural implants, prosthetics, surgical instruments and implements. Preferably, the invention includes impregnating or coating or covering items such as, without limitation, surgical gloves, catheters, artificial joints, breast implants, heart valves, pace makers and so on in the peptides of the present invention. In another embodiment of the invention it is envisaged that the peptides of the present invention may be included in a cement or glue or wound dressing or matrix. These particular embodiments are particularly advantageous as the only truly effective way of treating an individual with an implanted medical device that is infected with for example *S. epidermidis* is in its removal. Thus it will be appreciated that the present invention, which can mitigate such infections, would offer immediate benefit to patients and clinicians alike and also have an impact on reducing hospital costs.

Preferably, the peptides of the present invention are used to coat or cover or at least provide an overlay for plastics items, for example and without limitation a polyethylene surface. In addition to providing a coating or covering metal surfaces.

In a further embodiment of the invention the peptides of the present invention can be included in a dental preparation. Preferably, the dental preparation is selected from the group comprising a gel, spray, mouthwash, toothpaste, lozenge or chewing gum. It will be appreciated that a dental preparation containing the peptides of the present invention will be of particular utility in reducing the number of *Streptococcus mutans*, which are important causes of dental caries.

Accordingly in one aspect of the invention the peptides of the present invention are for use in the treatment of dental and gum diseases.

It will be appreciated that the present invention provides novel peptides and in particular peptides as depicted in any one of SEQ ID NOs: 1 to 8 that are modified and are originally derived from a Staphylococcal culture in which a peptide, located the structural gene of the peptide within producer designated 224, was isolated. The sequence QSFEWIYKQIKKLWA (SEQ ID NO:9) described in WO2011/073663, is a 15 residue amphipathic peptide which is predicted to adopt a α-helical conformation and demonstrates a net charge of +2. This peptide was used as a framework to generate multiple derivatives which included substituting and/or adding residues in order to increase either helical stability (for example the peptides of SEQ ID NO:1, SEQ ID NO:2 and SEQ ID NO:3) or overall charge (for example the peptides of SEQ ID NO:4, SEQ ID NO:5, SEQ ID NO:6, and SEQ ID NO:7); with the aim of increasing antimicrobial activity. It was surprising that despite significant changes i.e. more than 10% amino acid substitutions or additions to a peptide of only 15 residues results in modified non-natural peptide sequences that retained and in some case surpassed the bactericidal biological activity of the larger natural peptide. Indeed, irrespective of whether the modification was by substitution or conformational change the peptides of the present invention provide superior peptides insofar as they possess both Gram-negative activity and Gram positive activity and can be selected according to their potency to combat specific infections. Ideally, the peptides of the present invention may be used either in isolation or in combination according to the infection(s) that they are intended to combat in this way the peptides of the present invention can be tailored according to the disease and can be considered as designer peptides advantageously providing a wider or broader range of antibacterial activity The peptides described herein have significantly improved activity over those disclosed in WO2011/073663 as these new peptides have potent activity against Gram negative bacteria. This finding was un-expected and could not have been predicted based on data relating to inhibitory activity of the previous peptides. An additional observation of note is the possibility that these peptides can be specifically modified to form 'designer antibiotics' targeting defined species or genera. For example, in Table 2, it can be seen that peptide SEQ ID: No 3 has very low levels of activity (high inhibitory values) against most tested strains, but has good activity against *E coli* strains tested and could be said to have activity focused on *E coli*, rather than other Gram negative or Gram positive bacteria. The predicted secondary and tertiary structures of peptide SEQ ID: No3 are not dissimilar to those of other peptides in Table 3, so it would appear that more subtle amino acid sequence based changes may result in the targeted activity.

Example 1

Figure 1:
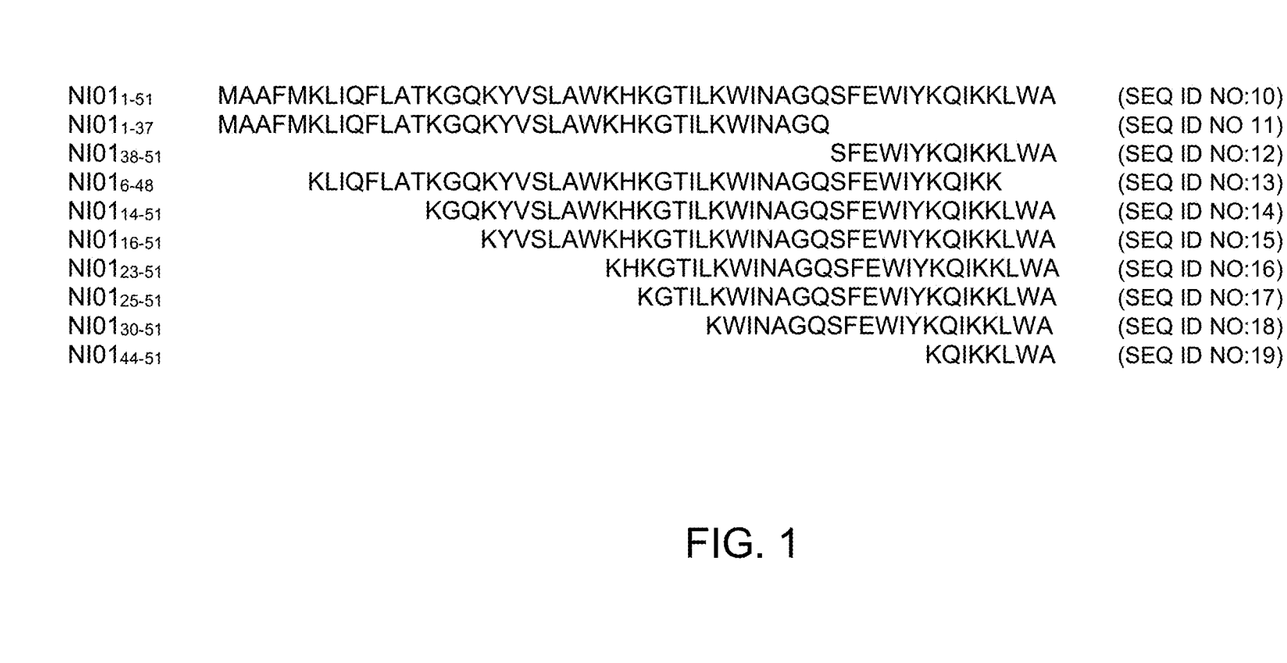
FIG. 1 shows truncated sequences (SEQ ID NOs: 11-19) of the full length epidermicin peptide (SEQ ID NO:10).

Experiments were conducted in which the full-length epidermicin peptide (51 amino acids, SEQ ID NO:10) was truncated to yield the derivatives shown in FIG. 1 (SEQ ID NOs:11 to 19). $NI01_{1-37}$ (SEQ ID NO:11) Is the region most similar to other peptides in the public domain, $NI01_{38-51}$ (SEQ ID NO:12) is the region that is most unique with respect to other peptides in the public domain. All other truncations have been carried out by removing residues from the amino-terminal end of the peptide to each lysine residue (K). Lysine is important in antimicrobial peptides as it contributes to the net positive charge, which is thought to have a key role in the mode of action of 'cationic' peptides, like NI01 (SEQ ID NO:10). These truncated peptides were tested for activity against Gram-positive bacteria, (Table 1), some of the truncations were observed to have retained potent activity against a range of target pathogens. From these results peptide $NI01_{38-51}$ (SEQ ID NO:12) was shown to retain surprising potency, given the length of 14 residues. This also suggests that the C-terminal part of the full length NI01 peptide is key for antimicrobial activity.

TABLE 1

Minimum inhibitory concentrations (MIC) of epidermicin NI01 derivatives against a range of gram-positive pathogens.

| | MIC (ug/ml) | | | | | | | | | |
|---|---|---|---|---|---|---|---|---|---|---|
| Peptide identifier with NI01 residues* (SEQ ID NO:) | $NI01_{1-51}$ (10) | $NI01_{1-37}$ (11) | $NI01_{38-51}$ (12) | $NI0_{6-48}$ (13) | $NI01_{14-51}$ (14) | $NI01_{16-51}$ (15) | $NI01_{23-51}$ (16) | $NI01_{25-51}$ (17) | $NI01_{30-51}$ (18) | $NI01_{44-51}$ (19) |
| *S. epidermidis* 1 | 0.63 | 12 | 6 | 16 | 16 | 12 | 16 | 4 | 4 | >64 |
| *S. epidermidis* 2 | 0.32 | 16 | 6 | 16 | 16 | 8 | 16 | 8 | 4 | >64 |
| *S. epidermidis* 37 | 0.10 | 16 | 6 | 32 | 12 | 8 | 16 | 8 | 4 | >64 |
| *S. epidermidis* 44 | 0.32 | 16 | 6 | 32 | 16 | 12 | 16 | 8 | 4 | >64 |
| *S. epidermidis* 60 | 0.32 | 24 | 6 | 32 | 16 | 8 | 16 | 16 | 6 | >64 |
| *S. epidermidis* 93 | 0.01 | 8 | 2 | 10 | 6 | 6 | 3 | 2 | 4 | >64 |
| Vanc. resistant *Enterococcus* 1 | 0.03 | 8 | 2 | 8 | 4 | 4 | 8 | 8 | 4 | >16 |
| Vanc. resistant *Enterococcus* 2 | 0.03 | 8 | 2 | 8 | 4 | 4 | 8 | 4 | 4 | 16 |
| Vanc. resistant *Enterococcus* 3 | 0.01 | 8 | 2 | 8 | 4 | 4 | 8 | 4 | 4 | 16 |
| Vanc. resistant *Enterococcus* 4 | 0.02 | 8 | 4 | 8 | 4 | 4 | 8 | 8 | 4 | 16 |
| Vanc. resistant *Enterococcus* 5 | 0.03 | 8 | 2 | 4 | 4 | 2 | 4 | 8 | 4 | 16 |
| Vanc. resistant *Enterococcus* 6 | 0.03 | 8 | 2 | 8 | 4 | 4 | 8 | 4 | 4 | 16 |
| *S. saprophyticus* | 0.02 | 8 | 4 | 8 | 8 | 4 | 8 | 4 | 4 | 16 |
| *S. aureus* 1195 | 0.16 | 8 | 4 | 8 | 8 | 8 | 8 | 8 | 8 | 16 |

TABLE 1-continued

Minimum inhibitory concentrations (MIC) of epidermicin NI01 derivatives against a range of gram-positive pathogens.

| | MIC (ug/ml) | | | | | | | | | |
|---|---|---|---|---|---|---|---|---|---|---|
| Peptide identifier with NI01 residues* (SEQ ID NO:) | $NI01_{1-51}$ (10) | $NI01_{1-37}$ (11) | $NI01_{38-51}$ (12) | $NI0_{6-48}$ (13) | $NI01_{14-51}$ (14) | $NI01_{16-51}$ (15) | $NI01_{23-51}$ (16) | $NI01_{25-51}$ (17) | $NI01_{30-51}$ (18) | $NI01_{44-51}$ (19) |
| S. Hominis | 0.42 | 12 | 4 | 16 | 6 | 6 | 4 | 16 | 6 | >64 |
| MRSA 37 | 0.03 | 12 | 12 | 32 | 16 | 8 | 12 | 8 | 6 | >64 |
| MRSA 71 | 0.03 | 8 | 12 | 24 | 12 | 12 | 12 | 4 | 6 | >64 |
| MRSA 42 | 0.03 | 12 | 12 | 24 | 12 | 8 | 12 | 4 | 8 | >64 |

*residue numbers in subscript indicate the regions of full-length NI01 peptide ($NI01_{1-51}$) that each derivative is comprised of (and relate to the scheme detailed above in "Derivitisation of epidermicin NI01").

Example 2

A series of derivatives of the $NI01_{38-51}$ (SEQ ID NO:12) truncation were carried out with a view to maintaining stability of the helix and/or increasing net positive charge of the peptides (Table 3). Table 3 also lists the rationale behind each modification. Minimum inhibitory concentrations (MICs) were determined for each derivative against a range of Gram positive and Gram negative organisms by a modified 2-fold microtitre broth dilution method (Wu and Hancock, J Biol Chem 1999; 274: 29-35) (Table 2). Previous data (not presented here) indicated that the full-length peptide (SEQ ID NO:10) did not have potent activity against Gram-negative bacteria (MIC values of >64 µg/ml were recorded). The activity of the derivatives referred to in Table 3 were tested against key drug-resistant Gram positive and negative pathogens and some, including $NI01_{38-51}$ (SEQ ID NO:12) and peptides SEQ ID NO: 4, 5, 6 and 7 all have potent activity against a broad spectrum of Gram positive and negative bacteria (Table 2). In contrast, the modifications made to peptides SEQ ID NO: 1, 2 and 3 significantly reduced activity (Table 2). This could not have been predicted. The activity of some peptides is more potent against strains of E coli, and the lack of activity of some derivatives indicates that the peptide $NI01_{38-51}$ (SEQ ID NO:12) has specific activity, not just a general lytic property. The data in Table 2 demonstrate the impact that some changes in sequence have on the potency of the derivative peptides and peptide SEQ ID NO:1 clearly has significantly reduced antimicrobial activity—this indicates that the lysine residue at position 10 is significantly associated with retention of activity. We have demonstrated that peptides only retaining 73% identity to peptide SEQ ID NO:12 ($NI01_{38-51}$) still exhibit antimicrobial activity against Gram positive and negative bacteria (Tables 2 & 4).

In addition, in vitro toxicity testing (haemolysis assays) indicates a lack of toxicity at levels well above MIC for some peptides, indicating potential for a wide therapeutic window (Table 6). Peptide $NI01_{38-51}$ (SEQ ID NO:12), along with peptides SEQ ID NO: 4, 5 and 6, exhibit higher levels of haemolytic activity compared to full length NI01 (Table 5). Since increased net charge is known to be associated with higher levels of haemolysis, (Dhople and Nagaraj, Peptides 2005: 26: 217-225), this was not wholly unexpected. Interestingly however, despite a net charge of +5, peptide SEQ ID NO:7 actually demonstrated relatively low levels of haemolysis, which were similar to that of full length NI01 (Table 6).

Proline residues are known to introduce a kink within helical structures, a modification that has been shown to reduce haemolytic activity but not affect antibacterial efficacy (Dhople and Nagaraj, Peptides 2005: 26: 217-225). Four additional $NI01_{38-51}$ derivatives (SEQ ID NOs: 20-23) were generated by the introduction of Proline, both alone and in combination with Lysine. These changes were intended to lower haemolytic activity in the derivatives with increased net charge without, any reducing the high activity levels previously obtained (particularly SEQ ID NO:4 and 5). However, a marked decrease in efficacy was observed for all such peptides. These results suggest that helicity, even more than net positive charge, is extremely important for antibacterial activity.

Table 3 shows percentage of sequence identity to SEQ ID NO:9 with regard to SEQ ID NOs:1, 7 and 8. The closest percentage identity is 86.6% and the most remote 73%. It was also determined that the residue essential to maintain potency, which therefore cannot be modified, is amino acid 11 in the sequence (K, lysine) and providing this key amino acid is retained the peptides of the present invention encompass a number of variants.

TABLE 2

Minimum inhibitory concentrations (MIC) of epidermicin NI01 derivatives against a range of Gram-positive and negative pathogens.

| | MIC (ug/ml) | | | | | | | | | | | |
|---|---|---|---|---|---|---|---|---|---|---|---|---|
| Isolate SEQ ID 4 | 12 | 2 | 1 | 3 | 4 | 5 | 6 | 7 | 20 | 21 | 22 | 23 |
| S aureus 1195 | 4 | 9 | >64 | 13 | 1.7 | 1.2 | 3.3 | 1.7 | >64 | 42.7 | 16 | 8 |
| MRSA 227 | 8 | 16 | >64 | >64 | 1.7 | 2 | 5.3 | 3.3 | >64 | >64 | 64 | 64 |
| MRSA 226 | 8 | 37.3 | >64 | 37.3 | 1.5 | 2 | 4 | 2.3 | >64 | 64 | 53.3 | 42.7 |
| MRSA 225 | 8 | 21.3 | >64 | >64 | 1.5 | 2.7 | 10.7 | 6.7 | >64 | >64 | 64 | 64 |
| MRSA 224 | 4 | 21.3 | >64 | 16 | 1.4 | 1.7 | 3.3 | 2.7 | >64 | 64 | 42.7 | 16 |
| MRSA 158 | 12 | 42.7 | >64 | >64 | 1.7 | 2 | 10.7 | 10.7 | >64 | >64 | >64 | 64 |
| VISA NRS36 | 42.7 | 53.3 | >64 | >64 | 5.3 | 8 | >64 | 16 | >64 | >64 | >64 | >64 |
| VISA NRS37 | 13.3 | 21.3 | >64 | 53.3 | 3.3 | 6.67 | >64 | 6 | >64 | >64 | >64 | >64 |
| VISA NRS39 | 53.3 | 64 | >64 | >64 | 3.3 | 6.67 | >64 | 16 | >64 | >64 | >64 | >64 |
| VISA NRS49 | 34.6 | 45.3 | >64 | 64 | 9.3 | 6 | >64 | 45.3 | >64 | >64 | >64 | >64 |
| P. aeruginosa | 64 | >64 | >64 | >64 | 6.7 | 4 | 32 | 8 | >64 | >64 | 64 | >64 |

TABLE 2-continued

Minimum inhibitory concentrations (MIC) of epidermicin NI01 derivatives against a range of Gram-positive and negative pathogens.

| Isolate SEQ ID 4 | MIC (ug/ml) | | | | | | | | | | |
|---|---|---|---|---|---|---|---|---|---|---|---|
| | 12 | 2 | 1 | 3 | 4 | 5 | 6 | 7 | 20 | 21 | 22 | 23 |
| P. aeruginosa 175 | 64 | >64 | >64 | >64 | 6.7 | 3.3 | 32 | 8 | >64 | >64 | 64 | >64 |
| E. coli DH5α | 8 | 17 | >64 | 9 | 1.5 | 2 | 6.7 | 4 | >64 | 26.7 | 10.7 | 13.3 |
| E. coli 50 | 7 | 27 | >64 | 11 | 2.3 | 1.3 | 4 | 4.3 | >64 | 64 | 42.7 | 18.7 |
| E.coli 177 | 5 | 19 | >64 | 5 | 2 | 2 | 4 | 3 | >64 | 53.3 | 13.3 | 16 |
| E. coli 178 | 5 | 27 | >64 | 21 | 1.3 | 1.3 | 8 | 3.3 | >64 | 64 | 32 | 26.7 |
| Klebsiella 4 | 27 | 48 | >64 | >64 | 3.3 | 2 | 10.7 | 8 | >64 | >64 | 64 | >64 |
| Klebsiella 5 | 32 | 64 | >64 | >64 | 6.7 | 8 | 10.7 | 13.3 | >64 | >64 | >64 | >64 |
| Klebsiella 7 | 21 | 64 | >64 | >64 | 4.7 | 4.7 | 10.7 | 10.7 | >64 | >64 | >64 | >64 |
| Klebsiella 13 | 21 | 37 | >64 | >64 | 3.3 | 2.7 | 10.7 | 18.7 | >64 | >64 | >64 | >64 |
| N. lactamica | 10.6 | 37.3 | >64 | >64 | 6.7 | 4.7 | 21.3 | 37.3 | x | x | x | x |

TABLE 3

Figure 2A:
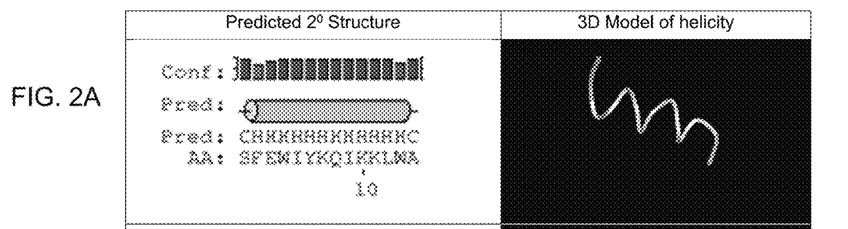
FIGS. 2A-2L show the predicted structures and 3D models of the peptides as described in Example 4 and Table 3.
Figure 2B:
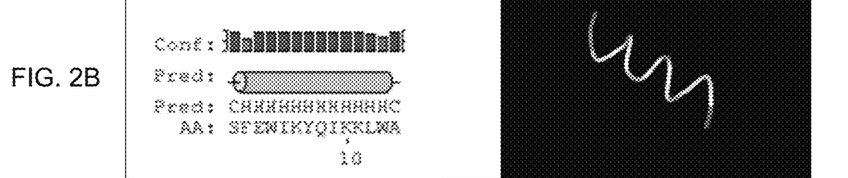
Figure 2C:
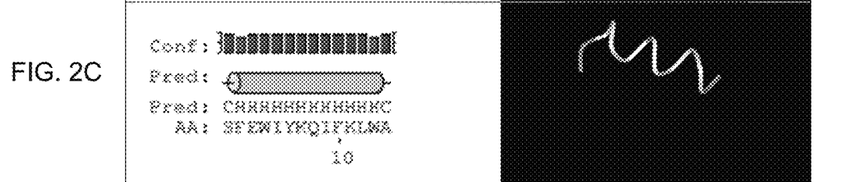
Figure 2D:
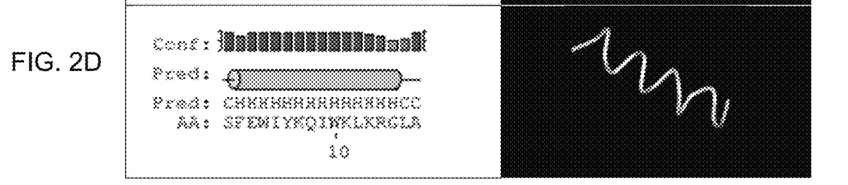
Figure 2E:
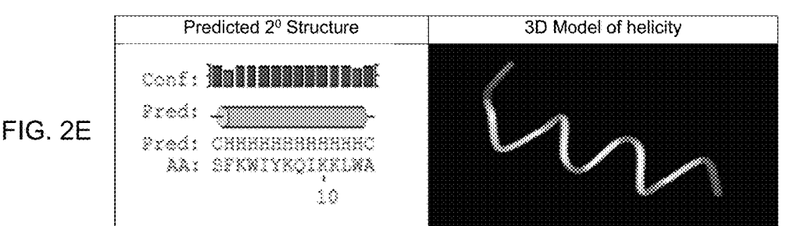
Figure 2F:
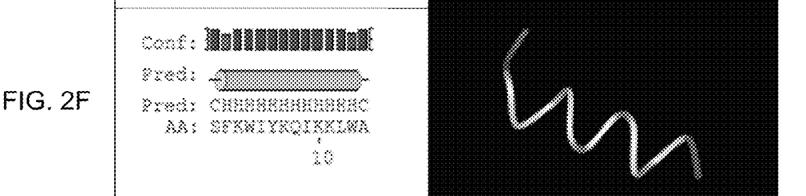
Figure 2G:
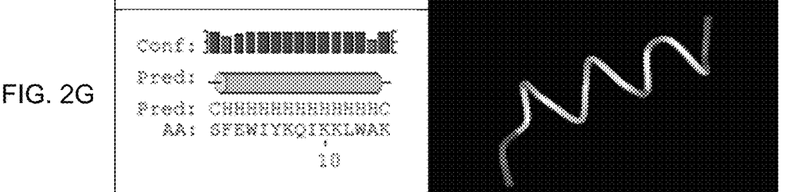
Figure 2H:
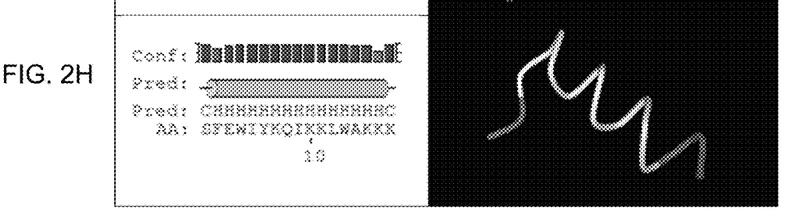

| Peptide | SEQ ID No | Sequence | Net Charge | Modification | Predicted 2° Structure and 3D Model of helicity |
|---|---|---|---|---|---|
| NI01 38-51 | 12 | SFEWIYKQIKKLWA | +2 | — | See FIG. 2A |
| MM02 | 2 | SFEWIKYQIKKLWA | +2 | Positions of K and Y (at positions 6 & 7) were switched to remove unfavourable electrostatic interactions between Lysine's at i + 3 and i + 4 distances thus stabilising the helix. | See FIG. 2B |
| MM05 | 1 | SFEWIYKQIFKLWA | +1 | K at position 10 was replaced with F to introduce aromatic interactions with the Y at position 6 (i + 4) and the W at position 13 (i + 3). Such interactions are thought to be helix stabilising. | See FIG. 2C |
| MM08 | 3 | SFEWIYKQIWKLKRGLA | +3 | Addition of a Schellman motif at the C-terminus. This introduces 2x H-bonds and 1x hydrophobic interaction across the cap of the helix, thus stabilising the structure. A Schellman motif requires at least one of C2, C3 or C4 to be apolar, C1 must be polar, C' must be Glycine, C'' must be hydrophobic for interaction with C2, C3 or C4, and C''' must be non-bulky. W and K at positions 10 and 13 were switched to introduce a polar residue (K) at C1. G, L and A were added to occupy C', C'' and C''' respectively. R was added at the C-cap to improve amphipathicity. | See FIG. 2D |
| MM011 | 5 | SFKWIYKQIKKLWA | +4 | Replacement of negatively charged E with positively charged K at position 3. Net charge is thus increased from +2 to +4. | See FIG. 2E |
| fMM011 | 4 | formyl-SFKWIYKQIKKLWA | +4 | As MM011 above. An N-terminal formylation has also been added. | See FIG. 2F |
| MM022 | 6 | SFEWIYKQIKKLWAK | +3 | Addition of 1K residue at the C-terminus which increases the Net Charge from +2 to +3. | See FIG. 2G |
| MM023 | 7 | SFEWIYKQIKKLWAKKK | +5 | Addition of 3K residues at the C-terminus which | See FIG. 2H |

TABLE 3-continued

Figure 2I:
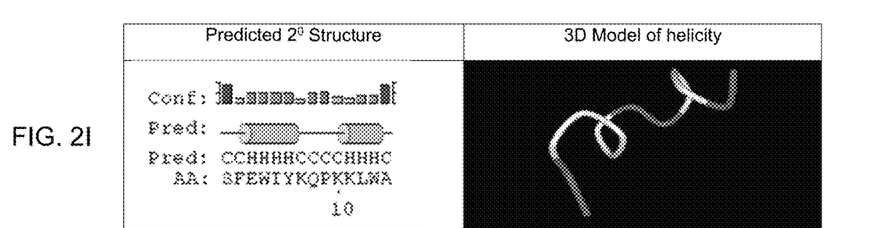
Figure 2J:
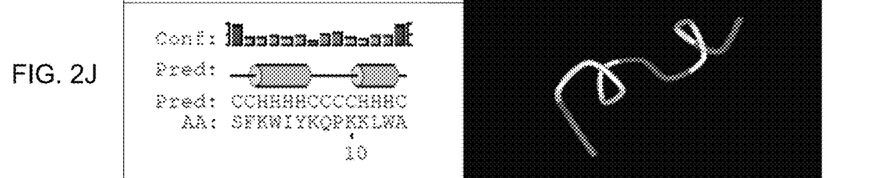
Figure 2K:
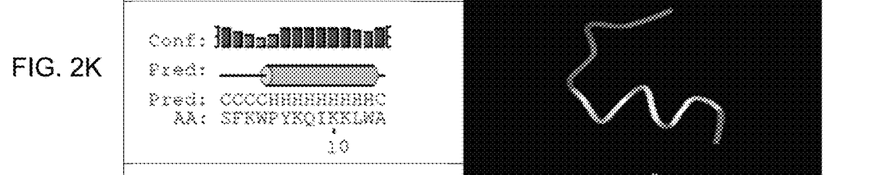
Figure 2L:
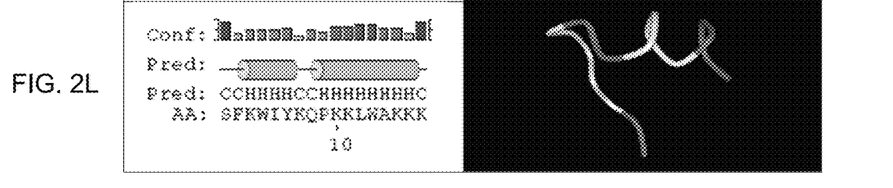

| Peptide | SEQ ID No | Sequence | Net Charge | Modification | Predicted 2° Structure and 3D Model of helicity |
|---|---|---|---|---|---|
| | | | | increases the Net Charge from +2 to +5. | |
| MM024 | 20 | SFEWIYKQPKKLWA | +2 | Isoleucine at position 9 has been replaced by Proline. | See FIG. 2I |
| MM025 | 21 | SFKWIYKQPKKLWA | +4 | Replacement of negatively charged E with positively charged K at position 3. Net charge is thus increased from +2 to +4. In addition Isoleucine at position 9 has been replaced by Proline. (MM011 + Proline at p9) | See FIG. 2J |
| MM026 | 22 | SFKWPYKQIKKLWA | +4 | Replacement of negatively charged E with positively charged K at position 3. Net charge is thus increased from +2 to +4. In addition Isoleucine at position 5 has been replaced by Proline. (MM011 + Proline at p5) | See FIG. 2K |
| MM027 | 23 | SFKWIYKQPKKLWAKKK | +7 | Replacement of negatively charged E with positively charged K at position 3 and addition of 3K residues at the C-terminus. Net charged is thus increased from +2 to +7. Isoleucine at position 9 has been replaced by Proline. (MM011 + MM023 + MM024). | See FIG. 2L |

TABLE 4

| Peptide | Sequence | Percentage Identical to Original |
|---|---|---|
| SEQ ID NO: 9 | QSFEWIYKQIKKLWA | N/A |
| Derivative peptide NI01$_{38-51}$ (SEQ ID NO: 12) | SFEWIYKQIKKLWA | 93% |
| Most dissimilar peptide with activity (SEQ ID NO: 7) | SFEWIYKQIKKLWAKKK | 73% |
| Most theoretically dissimilar peptide that we predict should have activity | SFEWXYKQXKKXWA* | 73% |

*X = Leucine or Isoleucine as these are generally interchangeable and most likely to have similar activity to the original (Alanine - although this is less hydrophobic than either Leucine or isoleucine and therefore may impact hydrophobic interactions as the X residues are at i + 3 and i + 4 positions from each other)

TABLE 5

Average MIC Data (ug/ml) for epidermicin derivative peptides against E. coli and K. pneumoniae

| Isolate | NI01$_{38-51}$ | MM02 | MM05 | MM08 |
|---|---|---|---|---|
| S aureus control | 4 | 9 | >64 | 13 |
| E. coli DH5a | 8 | 17 | >64 | 9 |
| E. coli 49 | 9 | 24 | >64 | 19 |
| E. coli 50 | 7 | 27 | >64 | 11 |
| E. coli 177 | 5 | 19 | >64 | 5 |
| E. coli 178 | 5 | 27 | >64 | 21 |
| E. coli 187 | 5 | 17 | >64 | 11 |
| K. pneumoniae 2 | 43 | 64 | >64 | >64 |
| K. pneumoniae 4 | 27 | 48 | >64 | >64 |
| K. pneumoniae 5 | 32 | 64 | >64 | >64 |
| K. pneumoniae 6 | 37 | 64 | >64 | >64 |
| K. pneumoniae 7 | 21 | 64 | >64 | >64 |
| K. pneumoniae 10 | 21 | 64 | >64 | >64 |
| K. pneumoniae 13 | 21 | 37 | >64 | >64 |

*Average of triplicate experiments

TABLE 6

Derivatives with Increased Charge - Haemolysis Assay
Percentage Haemolysis (Average of Triplicates)

| Peptide SEQ ID NO | Peptide Concentration (ug/ml) | | | | | | | | | | |
|---|---|---|---|---|---|---|---|---|---|---|---|
| | 400 | 200 | 100 | 50 | 25 | 12.5 | 6.25 | 3.125 | 1.562 | 0.78 | 0.39 | 0 |
| 12 | 111 | 110.2 | 79.4 | 46.1 | 26.2 | 6.8 | 3.4 | 1.4 | 0.7 | 0.6 | 0.5 | 0.6 |
| 4 | 111 | 83 | 55.3 | 36.98 | 17.98 | 7.2 | 3.5 | 1.6 | 1.1 | 0.6 | 0.5 | 0.6 |
| 5 | 109.8 | 75.4 | 52.4 | 29.9 | 13 | 6.8 | 3.4 | 1.8 | 1.3 | 1 | 1 | 0.6 |
| 6 | 104.9 | 65.3 | 46.8 | 23.6 | 8.7 | 3.7 | 2 | 1.1 | 1.1 | 0.6 | 0.6 | 0.9 |

TABLE 6-continued

Derivatives with Increased Charge - Haemolysis Assay
Percentage Haemolysis (Average of Triplicates)

| Peptide SEQ ID NO | Peptide Concentration (µg/ml) | | | | | | | | | | | |
|---|---|---|---|---|---|---|---|---|---|---|---|---|
| | 400 | 200 | 100 | 50 | 25 | 12.5 | 6.25 | 3.125 | 1.562 | 0.78 | 0.39 | 0 |
| 7 | 55.6 | 25.7 | 15.7 | 9.4 | 4.2 | 2.6 | 1.8 | 1.5 | 0.9 | 0.8 | 0.8 | 0.7 |
| NI01 | 47.2 | 26.96 | 18.1 | 10.8 | 7.8 | 3.7 | 2.3 | 1.5 | 0.7 | 0.7 | 0.3 | 0 |

Example 3

Experiments were conducted to assess the percentage haemolysis against peptide concentration for peptides SEQ ID NOs: 4, 5, 6 and 7 against full length epidermicin (SEQ ID NO:10) and SEQ ID NO:12. Table 6 shows the results over a concentration range of 0 to 400 µg/ml. A summary of the haemolysis data indicates lack of significant toxicity at 10×inhibitory concentrations and the low haemolytic activity is indicative that the peptides are possess specific bactericidal activity rather than exhibiting a lytic effect.

Example 4

Secondary structure predictions of the designed peptide derivatives were performed using Psipred (http://bioinf.cs.ucl.ac.uk/psipred/) in order to determine the likelihood of helix formation and what modifications would confer stability to the helix. Additionally, 3D models were generated using the Pepfold structure prediction programme (http://mobyle.rpbs.univ-paris-diderot.fr/cgi-bin/portal.py#forms::PEP-FOLD) followed by visualisation in Ugene. The predicted structures and 3D models are shown in FIGS. 2A-2L.

```
NI01 38-51 + 1K-SFEWIYKQIKKLWAK (charge +3) (MM022)
                                                      (SEQ ID NO: 6)
PSIPRED HFORMAT (PSIPRED V3.2) Secondary Structure
Prediction
Conf: 957899999999829                                 C = Coil
Pred: C-H-H-H-H-H-H-H-H-H-H-H-H-C                    H = Helix
AA:   SFEWIYKQIKKLAWK NI01 38-51 E-to-K-SFKWIYKQIKKLWA (charge +4) (MM011)
                                                      (SEQ ID NO: 5)
PSIPRED HFORMAT (PSIPRED V3.2) Secondary Structure
Prediction
Conf: 95789999999859                                  C = Coil
Pred: C-H-H-H-H-H-H-H-H-H-H-H-H-C                    H = Helix
AA:   SFKWIYKQIKKLWA NI01 38-51 +3K-SFEWIYKQIKKLWAKKK (charge +5) (MM023)
                                                      (SEQ ID NO: 7)
PSIPRED HFORMAT (PSIPRED V3.2) Secondary Structure
Prediction
Conf: 95789999999987539                               C = Coil
Pred: C-H-H-H-H-H-H-H-H-H-H-H-H-C                    H = Helix
AA:   SFEWIYKQIKKLWAKKK
```

The invention claimed is:

1. An isolated or recombinant peptide comprising a sequence selected from the group consisting of SFEWIYKQIFKLWA [SEQ ID NO:1], SFEWIKYQIKKLWA [SEQ ID NO:2], SFEWIYKQIWKLKRGLA [SEQ ID NO:3], formyl-SFKWIYKQIKKLWA [SEQ ID NO:4], SFKWIYKQIKKLWA [SEQ ID NO:5], SFEWIYKQIKKLWAK [SEQ ID NO:6], and SFEWIYKQIKKLWAKKK [SEQ ID NO:7].

2. The isolated or recombinant peptide according to claim 1 further comprising an attachment selected from the group consisting of a marker moiety, and a tag.

3. An isolated or recombinant nucleic acid sequence comprising a sequence encoding a peptide comprising a sequence selected from the group consisting of SFEWIYKQIFKLWA [SEQ ID NO:1], SFEWIKYQIKKLWA [SEQ ID NO:2], SFEWIYKQIWKLKRGLA [SEQ ID NO:3], formyl-SFKWIYKQIKKLWA [SEQ ID NO:4], SFKWIYKQIKKLWA [SEQ ID NO:5], SFEWIYKQIKKLWAK [SEQ ID NO:6], and SFEWIYKQIKKLWAKKK [SEQ ID NO:7].

4. The isolated or recombinant nucleic acid according to claim 3 further comprising a sequence encoding any one or more of the attachments selected from the group consisting of a marker moiety, and a tag.

5. A pharmaceutical composition comprising one or more of the peptides of claim 1.

6. An item impregnated with, coated in or covered by one or more of the peptides according to claim 1, wherein the item is selected from the group consisting of a medical device, medical or dental instrument, medical or dental implement, prosthetic, implantable device or material, and tissue or wound dressing.

7. An item comprising a plastic or metal surface impregnated with, coated in or covered with one or more of the peptides according to claim 1.

8. A biologically compatible material selected from the group consisting of cement, glue, composite, tissue matrix, tissue scaffold and wound dressing incorporating or impregnated with one or more of the peptides according to claim 1.

9. A dental preparation comprising one or more of the peptides of claim 1.

10. The dental preparation according to claim 9 selected from the group consisting of a spray, mouthwash, gel, paste, lozenge and chewing gum.

* * * * *